US006406874B1

(12) United States Patent
Kim et al.

(10) Patent No.: US 6,406,874 B1
(45) Date of Patent: Jun. 18, 2002

(54) METHOD OF DETERMINING THE ENZYMATIC ACTIVITY OF THE BLOOD COAGULATION FACTOR XIII USING PURIFIED FIBRIN MONOMER AS A SUBSTRATE

(75) Inventors: Hee-Chul Kim, Seoul; Jae-Wook Huh, Kyoungki-do; Shin-Jae Chang, Kyoungki-do; Jeung-Sik Lee, Kyoungki-do; Soon-Kwan Chung, Kyoungki-do; Hark-Mo Seong, Choongchongbuk-do, all of (KR)

(73) Assignee: Korea Green Cross Corporation, Kyonggi-do (KR)

( * ) Notice: Subject to any disclaimer, the term of this patent is extended or adjusted under 35 U.S.C. 154(b) by 0 days.

(21) Appl. No.: 09/242,436

(22) PCT Filed: Jun. 16, 1998

(86) PCT No.: PCT/KR98/00160

§ 371 (c)(1),
(2), (4) Date: Feb. 17, 1999

(87) PCT Pub. No.: WO98/58078

PCT Pub. Date: Dec. 23, 1998

(30) Foreign Application Priority Data

Jun. 18, 1997 (KR) ............................................. 97-25516

(51) Int. Cl.⁷ ................................................. C12Q 1/56

(52) U.S. Cl. ........................................... 435/13; 436/69
(58) Field of Search ............................... 435/13; 436/69

(56) References Cited

U.S. PATENT DOCUMENTS

| | | | |
|---|---|---|---|
| 5,508,202 A | | 4/1996 | Enomoto et al. |
| 5,552,296 A | * | 9/1996 | Adema et al. ................. 435/13 |
| 5,620,688 A | * | 4/1997 | Reed et al. ............... 424/145.1 |
| 5,723,126 A | * | 3/1998 | Gargan et al. ........... 424/145.1 |

FOREIGN PATENT DOCUMENTS

| | | |
|---|---|---|
| WO | 9004038 | 4/1990 |
| WO | 9210761 | 6/1992 |

* cited by examiner

*Primary Examiner*—Ralph Gitomer
(74) *Attorney, Agent, or Firm*—Backman & LaPointe, P.C.

(57) ABSTRACT

The present invention relates to a method of determining the enzymatic activity of blood coagulation factor XIII by using purified fibrin monomer as a substrate of this enzyme. The enzymatic activity is determined by detecting the degree of cross-linking of fibrin monomer formed by the blood coagulation factor XIII and the fibrin monomer free of blood coagulation factor XIII is obtained by washing the preparation with citric acid solution. The present method can be effectively used for the validation of the other enzymatic assay methods for the blood coagulation factor XIII as well as the studies for the characterization of the blood coagulation factor XIII.

6 Claims, 5 Drawing Sheets

METHOD OF DETERMINING THE ENZYMATIC ACTIVITY OF THE BLOOD COAGULATION FACTOR XIII USING PURIFIED FIBRIN MONOMER AS A SUBSTRATE

FIELD OF THE INVENTION

The present invention relates to a method of determining the enzymatic activity of the blood coagulation factor XIII using purified fibrin monomer as a substrate. Particularly, the present invention relates to a method of determining the enzymatic activity of the blood coagulation factor XIII by detecting the degree of fibrin cross-linking formed by the blood coagulation factor XIII, using fibrin monomer as a substrate, which are free of blood coagulation factor XIII.

BACKGROUND OF THE INVENTION

The blood coagulation factor XIII, circulating in the blood as a zymogen, is activated by thrombin in the presence of calcium ion and it is one of the transglutaminase which catalyzes an acyl transfer reaction. The blood coagulation factor XIII catalyzes the covalent cross-linking of the fibrin molecules by forming the isopeptide bridge between lysine and glutamine residues of fibrin molecules. The substrates having specificity to the blood coagulation factor XIII are usually intra-platelet substances, monocyte, macromolecules on the surface of epithelial cells or macromolecules circulating in blood: fibrin—fibrin; fibrin—fibrin (fibrinogen); fibrin—α2-plasminogen inhibitory factor; fibrin—fibronectin; fibrinogen—collagen; fibrin—von Willebrand factor; thrombospondin—thrombospondin; blood coagulation factor V—actin; von Willebrand factor—collagen; fibronectin—myosin; actin—myosin; gelsollin—fibrin or gelsollin; vincullin—fibrin (Karges, H. E., Clemens, R., *Behring Inst. Mitt.* 82: 43–58, 1988).

The blood coagulation factor XIII plays a role in hemostasis and wound healing process by forming fibrin clot which has strong mechanical strength and has an effect on cell proliferation, growth and metastasis of tumor cell and arteriosclerosis. It is known that the concentration of the blood coagulation factor XIII changes variously according to different pathologic states (inherited and acquired bleeding disease, chronic renal failure, malignant tumor, liver disease).

Since the blood coagulation factor XIII plays an important role in physiological field and the concentration of the blood coagulation factor XIII changes variously in different pathologic states, pathologic diagnosis by determining the enzymatic activity of the blood coagulation factor XIII is increasingly required in the clinical field. In addition, the assay method determining the enzymatic activity of the blood coagulation factor XIII is required in the inspection of pharmaceuticals containing the blood coagulation factor XIII as an effective agent. The assay method is also required for studying the characteristics of blood coagulation factor XIII.

Many previous techniques for the quantification method of the blood coagulation factor XIII have been developed which are, for example, clot lysis, SDS-PAGE of cross-linked fibrin, thromboelastography, binding of labeled or unlabeled amine, formation of ammonia in transamidation, detection of synthesized material and immunoassay (Karges, H. E., Clemens, R., *Behring Inst. Mitt.* 82: 43–58, 1988). But a rapid and simple assay method suitable for ordinary analysis has not been developed.

The conventional clot lysis method determines the enzymatic activity of the blood coagulation factor XIII in sample. The basis of this method is that, when dissolving agent (1% monocloroacetic acid) is added to fibrin clot, the enzymatic activity of the blood coagulation factor XIII in standard plasma diluted by minimal concentration (endpoint) enabling fibrin clot insoluble against dissolving agent, is same as the enzymatic activity of the blood coagulation factor XIII in sample diluted by maximal dilution factor making insoluble fibrin clot (Fibrin clot is formed by adding thrombin/calcium solution to the standard plasma (including blood coagulation factor XIII) and the sample, respectively diluted in appropriate dilution factor.). Therefore, the concentration (mU/ml) of the blood coagulation factor XIII in sample is calculated by multiplying the concentration of the blood coagulation factor XIII in standard plasma by dilution factor of sample making insoluble fibrin clot.

This assay method is simple, does not require expensive equipments and is easily used for determining the enzymatic activity of the blood coagulation factor XIII in clinical laboratories. However, there are problems in this method that the tight binding of the blood coagulation factor XIII to fibrinogen makes it difficult to remove the blood coagulation factor XIII from fibrinogen and that the blood coagulation factor XIII-free fibrinogen, the substrate of clot lysis method, is considerably expensive.

Accordingly, the present inventors have intensively studied to achieve a new simple method with reproducibility which can determine the enzymatic activity of the blood coagulation factor XIII rapidly and economically. This invention was completed by confirming that the enzymatic activity of the blood coagulation factor XIII can be determined economically and rapidly by detecting the degree of fibrin cross-linking formed by the blood coagulation factor XIII, using blood coagulation factor XIII-free fibrin monomer as a substrate.

SUMMARY OF THE INVENTION

The present invention provides a method of determining the enzymatic activity of the blood coagulation factor XIII by detecting the degree of fibrin crosslinking formed by the blood coagulation factor XIII using blood coagulation factor XIII-free fibrin monomer, as a substrate.

The present invention also provides a preparation method of fibrin monomer free of blood coagulation factor XIII by washing non-covalent fibrin polymer which is obtained from thrombin treated fibrinogen, with a suitable solution.

DETAILED DESCRIPTION OF THE INVENTION

Figure 1:
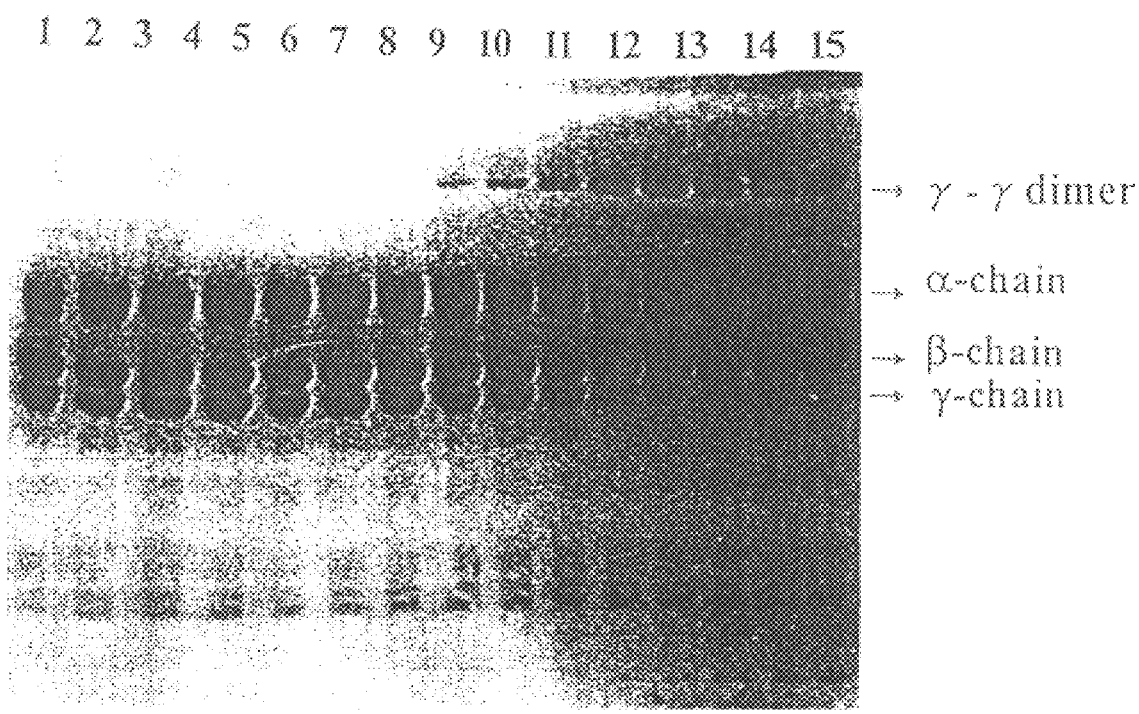
FIG. 1 is an electrophoregram of fibrin monomer preparations (10% SDS-polyacrylamide gel) which shows that exogenously adding the blood coagulation factor XIII catalyzes the fibrin monomer yielding γ—γ dimer. Lane 1, fibrin monomer; lanes 2–5, fibrin monomer preparations catalyzed by the blood coagulation factor XIII with increasing order of its concentration from 0 (lane 2) to 40 mU/ml (lane 15). All the fibrin monomer preparations were incubated with thrombin for the activation of the blood coagulation factor XIII for 1 hour at 37° C.

The present invention, firstly, deals with the preparation of highly purified fibrin monomer as a substrate of the blood coagulation factor XIII. In the present invention, purified fibrin monomer which is not containing blood coagulation factor XIII as a contaminant, is prepared by washing non-covalent fibrin polymer obtained from fibrinogen by thrombin treatment, with a suitable solution. Herein, the solution is preferably citrate solution.

The principle of the preparation of fibrin monomer which is completely free of blood coagulation factor XIII is described as follows.

Fibrinogen is dissociated into fibrin monomer and fibrinopeptide A, B, as a result of the proteolytic digestion by thrombin, wherein fibrin monomer, a soluble protein, is structurally well-arranged by hydrogen bond and converted into non-covalent fibrin polymer. By thorough washing of this non-covalent fibrin polymer with a suitable solution, the blood coagulation factor XIII which is tightly bound to fibrin polymer can be completely removed.

In the present invention, non-covalent fibrin polymer was produced from previously purified fibrinogen by the treatment with adequate amount of thrombin (preferably 25 U per 1 g of fibrinogen). It was dissolved with 5M urea solution, then dialyzed against 2 mM glacial acetic acid solution. After completing the dialysis, non-dissolved coagulation clot was removed by filtration.

The fact that the fibrin monomer preparation by the above process was completely free of blood coagulation factor XIII was subject to be verified by the absence of γ—γ dimer bands on SDS-polyacrylamide gel after the treatment of this preparation with thrombin and calcium chloride. The γ—γ dimer bands were not shown either in the fibrin monomer solution before the reaction or in the fibrin coagulation clot after the reaction, thus it was evident that blood coagulation factor XIII was completely removed from the fibrin monomer preparations of the present invention.

By determining the degree of fibrin cross-linking formed by blood coagulation factor XIII with above highly purified fibrin monomer as a substrate, the enzymatic activity of the blood coagulation factor XIII was determined. Likewise, transglutaminase activity can be determined by above process.

The principle of the method for the determination of the enzymatic activity of the factor XIII in the present invention is as follows.

The activated blood coagulation factor XIII by thrombin in the presence of calcium initially catalyzes the cross-linking of γ-chain into γ—γ dimer. This dimer is partially soluble, then gradually changes to insoluble polymer as α-chains form α-polymer. The rate of overall reaction is proportional to the enzymatic activity of the blood coagulation factor XIII, however the rate of formation of α-polymer is much slower than that of γ—γ dimer. This makes it possible to determine the enzymatic activity of the blood coagulation factor XIII.

In detail, the SDS-polyacrylamide electrophoresis gel of fibrin clot, the change of the ratio of the formed γ—γ dimer to γ-monomer, the measurement of absorbance of dissolved fibrin clot, the microplate method for blood coagulation factor XIII assay, clot lysis method and the like could be used as a method of determination of the concentration of the blood coagulation factor XIII.

In the present invention, as plasma sample was added to the fibrin monomer solution with increasing order of the dilution factor the cross-linking reaction took place in the presence of calcium and thrombin. Fibrin coagulation clot formed as a result of the above reaction was dissolved with urea solution and subjected to run on a SDS-polyacrylamide electrophoresis gel in order to detect formed γ—γ dimer band. Then, the enzymatic activities of the blood coagulation factor XIII in the samples were determined in comparison with standard plasma of known of blood coagulation factor XIII activity.

Similarly, they could be obtained from the ratio of formed γ—γ dimer to γ-monomer which was determined by densitometric analysis of corresponding bands on a SDS polyacrylamide electrophoresis gel.

The absorbance of reaction resultant after dissolving the fibrin clot was measured in order to indicate the solubility of fibrin clot which is inversely proportional to the enzymatic activity of the blood coagulation factor XIII.

In the case of the microplate determination method, after the fibrin monomer coupled microplate was reacted with biotinylpentylamine as a substrate of blood coagulation factor XIII in the presence of calcium, thrombin. The enzymatic activity of the blood coagulation factor XIII was determined by measuring the amount of incorporation of biotinylpentylamine to fibrin monomer coupled microplate with a streptavidine conjugated peroxidase.

And the enzymatic activity of the blood coagulation factor XIII can be determined by conventional clot lysis method using purified fibrin monomer as a substrate.

In the present invention, by evaluating the reproducibility of this clot lysis method and examining the correlation of this method with $C^{14}$-putrescine incorporation method which is one of the method measuring the enzymatic activity of the blood coagulation factor XIII, it was confirmed that the present method had a excellent reproducibility and correlation with other method by showing that the coefficient of variance of intra- and inter assay were 3.7% and 5% respectively, and the coefficient of correlation with a $C^{14}$-putrescine incorporation method was 0.95 (p>0.01).

The materials used in the present invention are described as follows.

Materials comprise of 1M Tris-acetate (containing 125 mM calcium chloride, pH 8.0), 1% (w/v) monochloroacetic acid solution, standard plasma (blood coagulation factor XIII), diluent (0.4% albumin, 0.15M sodium chloride), kaolin, blood coagulation factor XIII free-fibrin monomer, thrombin solution (200 U/ml) and 2 mM glacial acetic acid. The materials such as 1M Trisacetate, 1% monochloroacetic acid solution, diluent, kaolin, lyophilized fibrin monomer and a 2 mM glacial acetic acid have to be stable for several months in the refrigerator. And standard plasma have to be stable at −70° C. and must be used within 4hours at room temperature.

Standard human plasma product from Behring was used as standard plasma (blood coagulation factor XIII); Thrombin, 20% albumin, fibrinogen was purchased from Korea Green Cross Co.; kaolin, monochloroacetic acid, trizma base, calcium chloride, sodium chloride, dialysis tubing (cut off value=12,000 Da), ε-aminocaproic acid (hereinafter referred to as "EACA") was from Sigma chemical Co.; urea was from ICN biochemical Co.; and glacial acetic acid and sodium citrate was from Riedel deHaen. The sample plasma used in this method was obtained from healthy individuals and stored at −20° C. until used.

The present invention is further illustrated with reference to the following examples which are not intended to be in any way limiting to the scope of the invention as claimed.

EXAMPLE 1

Preparation of Fibrin Monomers Free of Blood Coagulation Factor XIII

The precipitated fibrinogen by the glycine precipitation method was dissolved by immersing it in 0.05M citrate buffer solution (pH 5.5–8.0, preferably 6.8, 0.15M sodium chloride) for 1 hour at 4° C. After adjusting the protein concentration of this solution to 5 mg/ml, EACA was added into the fibrinogen solution (final concentration of 50 mM). The resulting solution was incubated for 30 minutes at room temperature. To precipitate the fibrinogen again solid glycine (150 g/l) was added to the solution. The precipitate was centrifuged (15,000×g, 30 minutes) . After the supernatant was decanted the pellet was dissolved with adequate volume of 50 mM citrate buffer to adjust the protein concentration to 10 mg/ml. To form fibrin clot, thrombin (25 U per 1 g of fibrinogen) was added into fibrinogen solution. The reaction mixture was incubated at 37° C. As soon as fibrin clot was formed, it was spooled with a glass rod and then minced with scissors. In order to remove completely any soluble proteins within the fibrin clot, minced fibrin clot was washed with the citrate buffer solution and centrifuged repeatedly (preferably 5 times). The washed pellet was immediately dissolved with 5M urea solution, preferably within 30 min, wherein the concentration of fibrinogen was adjusted over 13 mg/ml. The resulting solution was dialyzed against 2 mM glacial acetic acid solution. At the early stage of dialysis, precipitate was transiently formed as the urea concentration of inside the dialysis tubing was decreased, however it was gradually dissolved at the later stage of the dialysis. After non-dissolved debris were removed by filtration, the filtrate was lyophilized. Lyophilized fibrin monomer was stored at 4° C.

EXAMPLE 2

Examination on Fibrin Monomer Free of Blood Coagulation Factor XIII

To test whether or not the fibrin monomer solution prepared in accord to the example 1 retained the blood coagulation factor XIII activity as an indication of impurity, SDS-polyacrylamide electrophoresis gel was performed according to Laemmli method (*Nature*, 227: 680–685, 1970). If there is any enzymatic activity of the blood coagulation factor XIII in the fibrin monomer solution, γ—γ dimer band is formed in the presence of both thrombin and calcium chloride and can be detected on the SDS-polyacrylamide gel.

The lyophilized fibrin monomer was dissolved with 2 mM glacial acetic acid solution to get 1% (w/v) fibrin monomer solution and the standard plasma was diluted with diluent to get the final concentrations of the blood coagulation factor XIII as follows; 0, 0.028, 0.055, 0.11, 0.22, 0.44, 0.88, 1.75, 2.50, 5.00, 10.00, 20.00, 30.00 and 40.00 mU/ml, respectively. Then, 200 μl aliquots of the above diluted standard blood coagulation factor XIII were added into 10 ml glass test tubes, respectively. Kaolin was dissolved with diluent to get 0.6% (w/v) kaolin solution. The 200 μl of 200 U/ml thrombin solution, 2.2 ml of 0.6% kaolin solution and 0.8 ml of 1M Tris-acetate (containing 125 mM calcium chloride, pH 8.0) were mixed well to get the final concentration of 0.4M Tris-acetate, 50 mM calcium chloride, 10 U thrombin, pH 8.0. Then 100 μl aliquot of the above thrombin/calcium/kaolin solution was added into the above-mentioned 10 ml glass test tube. As soon as mixture was gently stirred, 100 μl of fibrin monomer solution was immediately added to the mixture. Then, the reaction mixture was gently stirred by hand 1–2 times and incubated for 1 hour at 37° C. Then, the formed fibrin clots were dissolved with 1 ml of 8M urea, and 30 μl of this solution was analyzed on 10% SDS-polyacrylamide electrophoresis gel in order to detect any γ—γ dimer band (FIG. 1).

Lane 1 is for fibrin monomer and lane 2–15 is for the fibrin monomer preparations catalyzed by activated blood coagulation factor XIII with increasing order of its concentration from 0 (lane 2) to 40 mU/ml (lane 15).

The γ—γ dimer bands were not shown either in the fibrin monomer solution before the reaction or in the fibrin clot after the reaction, thus it was evident that the blood coagulation factor XIII was completely removed from the fibrin monomer preparations of the example 1.

EXAMPLE 3

The Examination of Prepared Fibrin Monomer as a Substrate of the Blood Coagulation Factor XIII It was examined whether the fibrin monomer in accord to the example 1 could be used as a substrate of the blood coagulation factor XIII or not. After the reaction according to the procedure described in example 2 with various concentration of blood coagulation factor XIII, the ratio of formed γ—γ dimer to γ-monomer was determined by densitometric analysis of corresponding bands on an SDS polyacrylamide electrophoresis gel.

Figure 2:
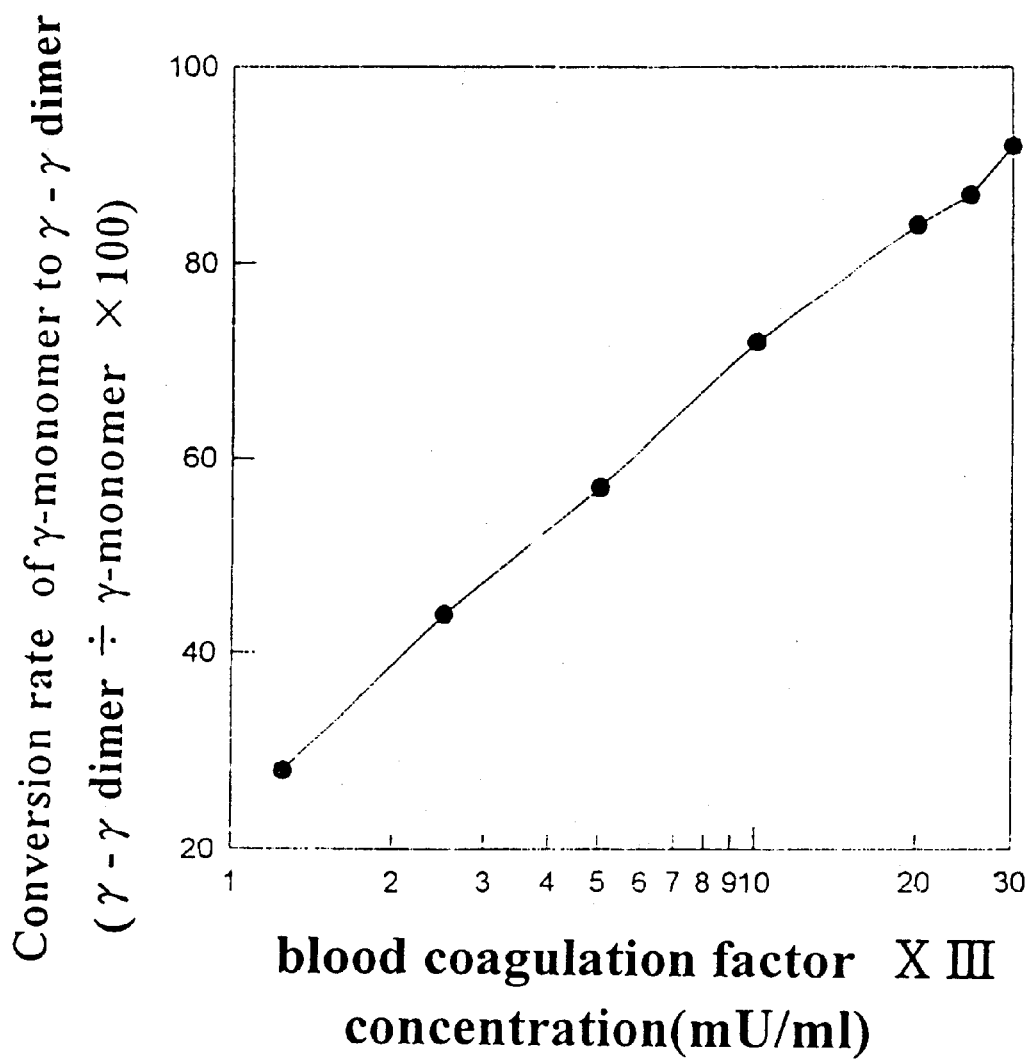
FIG. 2 depicts the decrease of the concentration of γ-chain and the increase of that of γ—γ dimer indicating that the fibrin monomer was catalyzed by the enzymatic reaction of the blood coagulation factor XIII.

FIG. 2 depicts the decrease of the concentration of γ-chain and the increase of that of γ—γ dimer indicating that the fibrin monomer was catalyzed by the enzymatic reaction of the blood coagulation factor XIII. The enzymatic activity of the blood coagulation factor XIII could be determined on the base of this fact.

Figure 3:
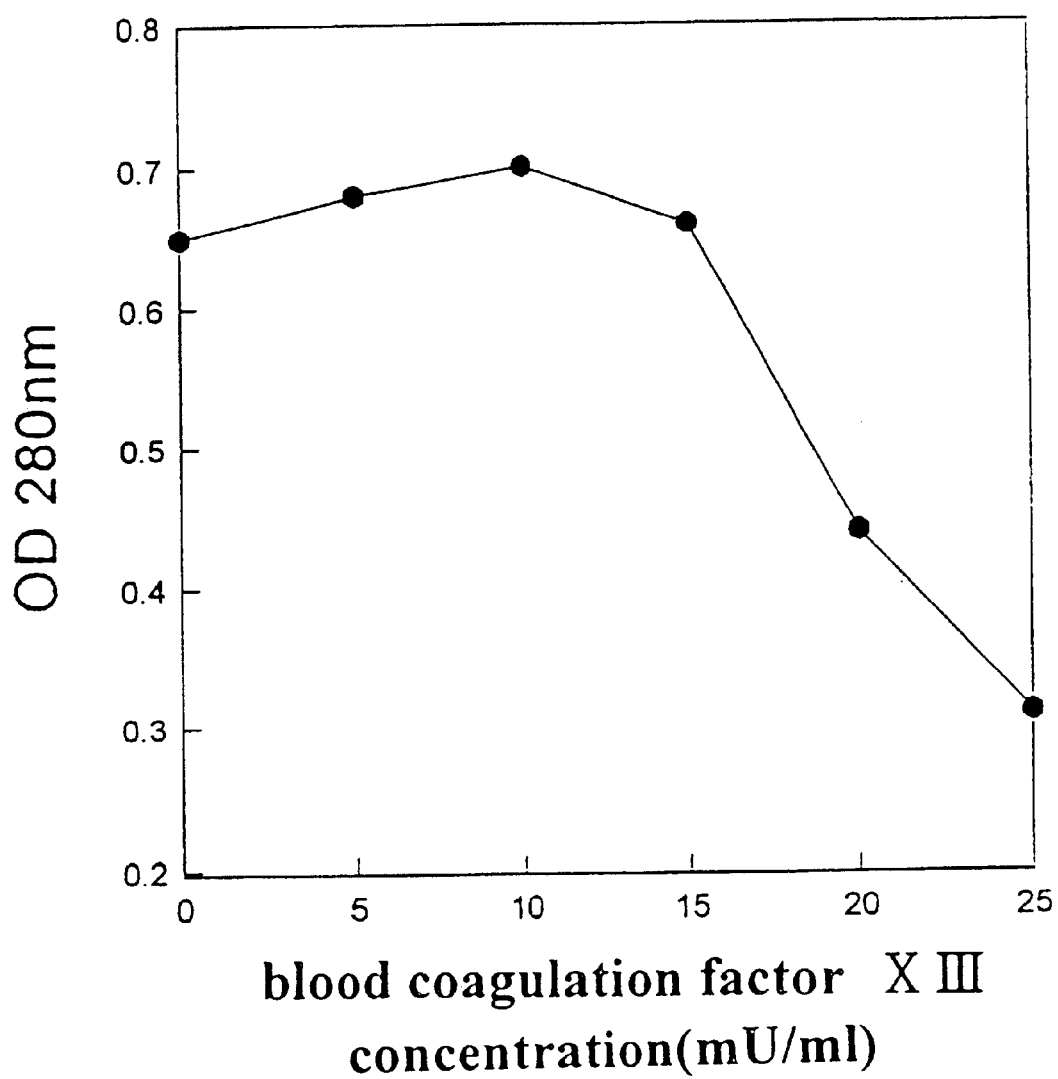
FIG. 3 shows the solubility of fibrin clot in 1% monochloroacetic acid solution, which is indicated as an optical density at 280 nm. The fibrin clot was previously formed by the reaction of fibrin monomer with the blood coagulation factor XIII.

In addition, after the reaction according to the method as described in example 2 with various concentration of the blood coagulation factor XIII, the formed fibrin clots were dissolved by addition of 3 ml of 1% monochloroacetic acid. After 5 min of the incubation, the optical density of resulting supernatants was measured at 280 nm. It appeared that the solubility of fibrin clot was inversely proportional to the enzymatic activity of the blood coagulation factor XIII (FIG. 3). Therefore, the enzymatic activity of the blood coagulation factor XIII could be determined on the base of this fact.

EXAMPLE 4

The Reproducibility of the Clot Lysis Assay Method and the Correlation of this Method With Other Blood Coagulation Factor XIII Assay Methods The reproducibility of the present clot lysis method was examined to verify whether or not the enzymatic activity values for the blood coagulation factor XIII could reliably be obtained by this assay method.

Due to the sensitivity range (the end point of 15–30 mU/ml) of this assay method, the blood coagulation factor XIII in normal human blood could be detected in the solution of about 10 to 70 fold dilution of the samples. The detection procedure is described as follows.

The lyophilized fibrin monomer was dissolved with 2 mM glacial acetic acid solution to get 1% (w/v) fibrin monomer solution. The sample was properly diluted from the range of 10-, 20-, 30-, 40-, 50-, 60-, and 70-fold with diluent and the standard plasma was diluted to get the blood coagulation factor XIII concentration of 12, 14, 16, 18, 20 and 22 mU/ml, respectively. Kaolin was dissolved with diluent to get 0.6% (w/v) kaolin solution. Then, 200 μl aliquots of the above diluted standards and samples were added into 10 ml glass test tubes, respectively. The 200 μl of 200 U/ml thrombin solution, 2.2 ml of 0.6% kaolin solution and 0.8 ml of 1M Trisacetate (containing 125 mM calcium chloride, pH 8.0) were mixed well to get the final concentration of 0.4M Trisacetate, 50 mM calcium chloride, 10 U thrombin, pH 8.0, and then 100 μl aliquot of the above thrombin/calcium/kaolin solution was added into the above-mentioned 10 ml glass test tubes. As soon as mixture was gently stirred, 100 μl of fibrin monomer solution was immediately added to the mixture. Then, the reaction mixture was gently stirred by hand 1–2 times and incubated for 1 hour at 37° C. Then 3 ml aliquots of 1% monochloroacetic acid were added to the formed fibrin clot. The mixture was hand-shaken in every 10 minutes for 30 minutes to dissolve the fibrin clot. For both samples and standard solutions the test tubes of the maximum dilution factor were selected among the test tubes which showed the remaining—not dissolved—fibrin clots. The concentration of the blood coagulation factor XIII in the selected test tube from the sample supposedly was identical to that in the selected test tube from standard. This concentration of the blood coagulation factor XIII is defined as the endpoint of the assay.

As a result, the endpoint (the minimal concentration of the blood coagulation factor XIII required for forming coagulation clot which was not dissolved by the 1% monochloroacetic acid) was 18 mU/ml. The coefficient of variance of intra—and inter assay were 3.7% and 5%, respectively, which represented that the present method had an excellent reproducibility (Table 1 and Table 2).

TABLE 1

The reproducibility of clot lysis assay (variance of intra assay)

| Mean endpoint (n = 10) | Standard deviation (SD) | Coefficient of variance (CV) |
|---|---|---|
| 18.2 mU | 0.667 | 3.7% |

TABLE 2

The reproducibility of clot lysis assay (variance of inter assay)

| Mean endpoint (n = 10) | Standard deviation (SD) | Coefficient of variance (CV) |
|---|---|---|
| 18.6 mU | 0.966 | 5% |

Figure 4:
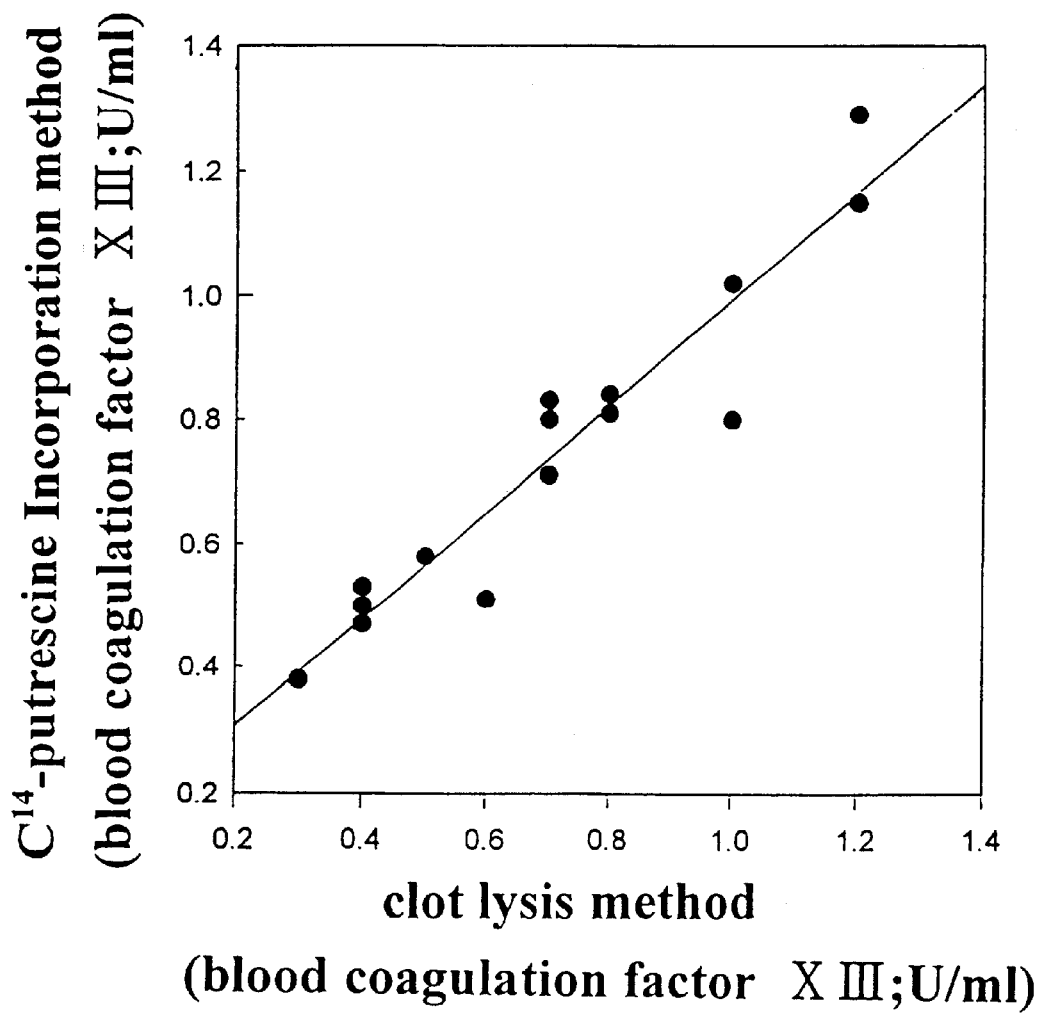
FIG. 4 shows the linear correlation (r=0.95, n=15) between the $C^{14}$ putrescine incorporation method as a conventional assay for blood coagulation factor XIII and the clot lysis method of the present invention.

In addition, as to the correlation with other blood coagulation factor XIII assay methods the present method showed high correlation with $C^{14}$-putrescine incorporation method (Chung S. I. And J. E. Folk, *J. Biol. Chem.* 247: 2798–2807, 1972) with a coefficient of correlation, 0.95 (p>0.01)(FIG. 4).

EXAMPLE 5

Microplate Determination Method Using Fibrin Monomer as a Substrate

The fibrin monomer was diluted to the concentration of lower than 100 μg/ml with coating buffer (50 mM carbonate buffer solution, pH 9.6). The aliquots of 150 μl of fibrin monomer solution were added to each well of microplate and incubated for 16 hours at room temperature for binding fibrin monomer to the microplate. The unbound fibrin monomer was removed by washing the microplate two times with 40 mM Tris buffer solution (0.15M sodium chloride, pH 8.3).

The remaining surface of the well of the microplate, which was not coated with the fibrin monomer, was blocked with 1% bovine serum albumin to prevent the surface from the nonspecific binding of other proteins. The prepared microplate was stored in refrigerator with/without lyophilization.

After the 50 μl aliquots of the standard blood coagulation factor XIII having the concentration of 0.25, 0.5, 1, 2, 4, 8 and 16 mU/ml were added into each well of the microplate which was pre-coated with fibrin monomer, the 45 μl aliquots of the mixture solution (10 μl of thrombin (10 U/ml), 15 μl of 5 mM biotinylpentylamine, 20 μl of 50 mM calcium chloride and 17.5 mM dithiothreitol) were added into each well and mixed gently. Then reaction mixture was incubated for 1 hour at room temperature. The binding reaction was stopped by addition of 20 μl of 0.2M EDTA (ethylene diamine tetraacetic acid).

After unbound biotinylpentylamine to the fibrin monomer was removed by washing three times with 40 mM Tris buffer solution, the 100 μl aliquots of the streptavidine conjugated horse-radish peroxidase solution diluted by 4000-fold were added into each well and incubated for 30 min at room temperature. Subsequently, the unbound streptavidine conjugated horse-radish peroxidase to the biotinylpentylamine was removed by washing five times with 40 mM Tris buffer.

The 100 μl aliquots of a substrate of horse-radish peroxidase were added into each well and incubated for 15 min at room temperature. Then the absorbance was measured at 405 nm (Lee, K. N., et al., *Clin. Chem.* 34: 906–910, 1988; Yeqing C. Song, et al., *Anal. Biochem.* 223: 88–92, 1994).

Figure 5:
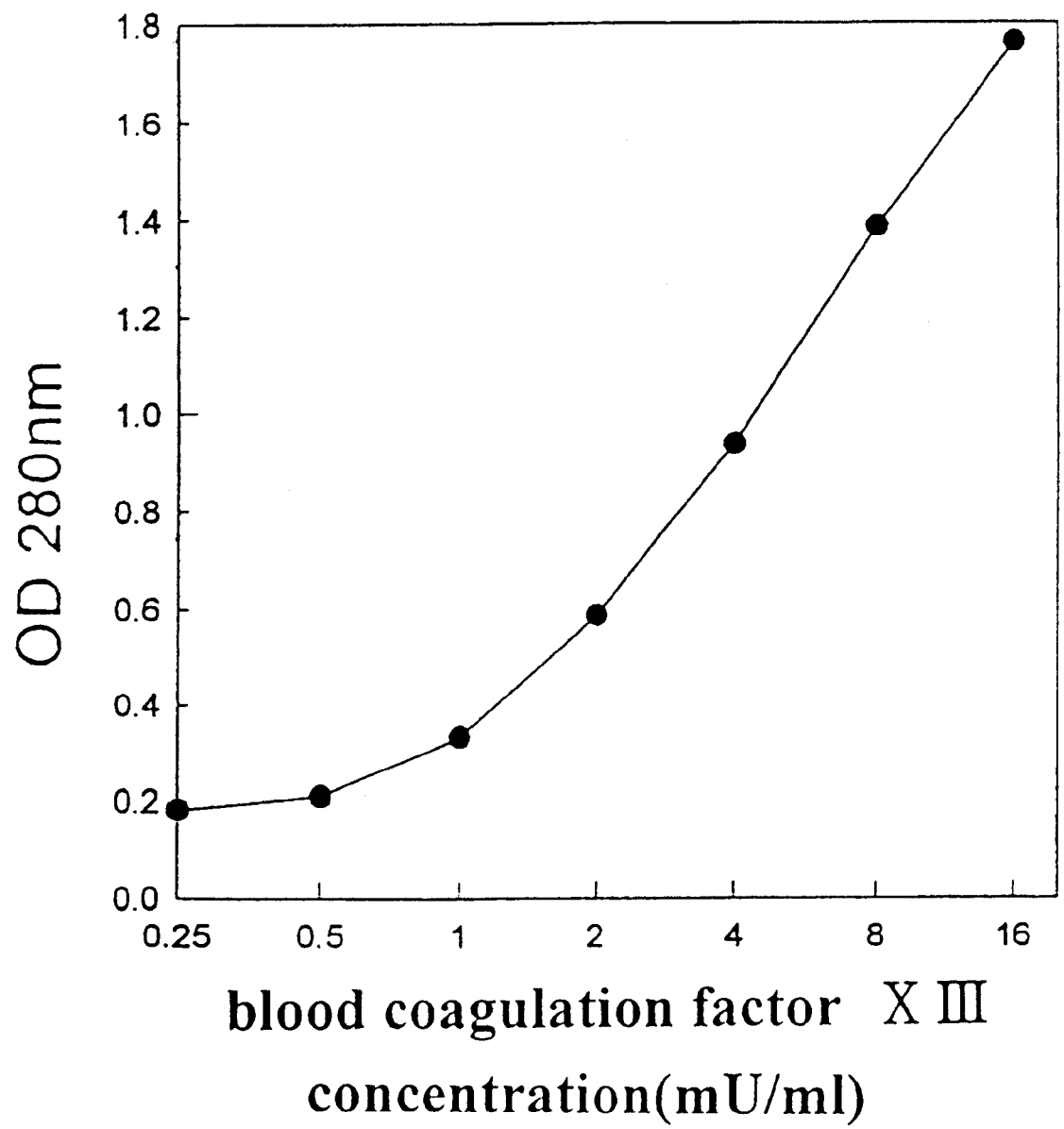
FIG. 5 shows the standard calibration curve for the concentration of the blood coagulation factor XIII obtained by using microplate method.

As a result, the linear correlation of the absorbance and blood coagulation factor XIII concentration was observed in the range of 1–10 mU/ml, therefore, the concentration of the blood coagulation factor XIII was able to be determined quantitatively within the above range (FIG. 5).

EFFECT OF THE INVENTION

In the present invention, the fibrin monomer free of blood coagulation factor XIII is used as a substrate in determining the enzymatic activity of the blood coagulation factor XIII. Since the fibrin monomer can be easily obtained in large amount, the present method is highly economical. In addition, the present method can be performed with an excellent reproducibility because fibrin monomer or fibrinogen is a natural substrate of the blood coagulation factor XIII.

Therefore, the present method using the fibrin monomer as a substrate of the blood coagulation factor XIII can rapidly and simply determine the enzymatic activity of the blood coagulation factor XIII with an excellent reproducibility. Moreover, the present invention can be used for the validation of the other enzymatic assay methods for the blood coagulation factor XIII as well as the studies for the characterization of the blood coagulation factor XIII.

What is claimed is:

1. A method of determining an enzymatic activity of blood coagulation factor XIII comprising the steps of:
   (1) reacting blood coagulation factor XIII with a purified fibrin monomer as a substrate which is free of contaminating blood coagulation factor XIII;
   (2) forming a fibrin clot;
   (3) detecting a degree of fibrin crosslinking in the clot; and
   (4) correlating the degree of fibrin crosslinking with the enzymatic activity of Factor XIII.

2. The method according to claim 1, wherein the enzymatic activity of blood coagulation factor XIII is determined by measuring a ratio of an amount of formed γ—γ dimer to that of γ-monomer after a reaction of the fibrin monomer with blood coagulation factor XIII, and the formed fibrin clot is examined on an SDS-polyacrylamide electrophoresis gel.

3. The method according to claim 1, wherein the enzymatic activity blood coagulation factor XIII is determined by measuring absorbance after the reaction of the fibrin monomer with blood coagulation factor XIII in the presence of thrombin and calcium chloride.

4. The method according to claim 1, wherein fibrin monomer is coated in a microplate.

5. The method according to claim 1, wherein the enzymatic activity of blood coagulation factor XIII is determined by checking an endpoint in a dilution-based assay.

6. The method according to any one of claims 1, 2, 3, 4 or 5, wherein the purified fibrin monomer free of contaminating blood coagulation factor XIII is prepared by washing a non-covalent fibrin polymer obtained from thrombin treated fibrinogen with a solution.

* * * * *